United States Patent
Mori

(10) Patent No.: US 7,326,189 B2
(45) Date of Patent: *Feb. 5, 2008

(54) ASSEMBLY OF WINGED NEEDLE AND PROTECTOR SHEATH FOR WINGED NEEDLE

(75) Inventor: Takeshi Mori, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/655,826

(22) Filed: Jan. 22, 2007

(65) Prior Publication Data

US 2007/0118082 A1 May 24, 2007

Related U.S. Application Data

(62) Division of application No. 10/804,031, filed on Mar. 19, 2004, now Pat. No. 7,175,610.

(30) Foreign Application Priority Data

Mar. 20, 2003 (JP) .............................. 2003-078867

(51) Int. Cl.
*A61M 5/00* (2006.01)
(52) U.S. Cl. ........................ 604/263; 604/171; 604/110
(58) Field of Classification Search ................ 604/263, 604/171, 177, 198, 110, 162, 164.01, 164.02, 604/164.04, 164.06, 164.07, 164.08, 164.11, 604/165.01, 165.02, 165.03
See application file for complete search history.

(56) References Cited

U.S. PATENT DOCUMENTS

| | | | |
|---|---|---|---|
| 4,842,586 A * | 6/1989 | Hogan | 604/192 |
| 4,941,881 A | 7/1990 | Masters et al. | 604/162 |
| 5,069,341 A | 12/1991 | Barbieri et al. | 206/365 |
| 5,112,311 A | 5/1992 | Utterberg et al. | 604/177 |
| 5,266,072 A | 11/1993 | Utterberg et al. | 604/177 |
| 5,330,438 A * | 7/1994 | Gollobin et al. | 604/177 |
| 5,562,636 A | 10/1996 | Utterberg | 604/263 |
| 5,562,637 A | 10/1996 | Utterberg | 604/263 |
| 5,704,917 A | 1/1998 | Utterberg | 604/180 |
| 5,772,638 A | 6/1998 | Utterberg et al. | 604/263 |
| 5,827,239 A | 10/1998 | Dillon et al. | 604/263 |
| 5,951,529 A | 9/1999 | Utterberg | 604/263 |
| 6,050,976 A | 4/2000 | Thorne et al. | 604/164 |

(Continued)

FOREIGN PATENT DOCUMENTS

JP 6-63137 A 3/1994

(Continued)

*Primary Examiner*—Kevin C. Sirmons
*Assistant Examiner*—Laura C. Schell
(74) *Attorney, Agent, or Firm*—Kubovcik & Kubovcik

(57) ABSTRACT

A protector sheath for winged needle capable of accommodating a winged needle having a needle tube with a sharp blade edge, a hub firmly attached to a proximal end portion of the needle tube, and a wing provided on the hub is provided. The protector sheath has a cylindrical main body, at least one slit is provided in a side wall of the main body, a proximal end portion of the slit is provided so as to be parallel to the axis of the main body, and a distal end portion of the slit is provided so as to extend in a direction which is not parallel to the axial direction of the main body.

10 Claims, 6 Drawing Sheets

U.S. PATENT DOCUMENTS 6,554,807 B2  4/2003  Gollobin .................... 604/263

FOREIGN PATENT DOCUMENTS

| JP | 7-75671 A | 3/1995 |
| JP | 8-206195 A | 8/1996 |
| JP | 2813886 B2 | 8/1998 |
| WO | 97/25082 A1 | 7/1997 |

* cited by examiner

ASSEMBLY OF WINGED NEEDLE AND PROTECTOR SHEATH FOR WINGED NEEDLE

This application is a divisional of U.S. patent application Ser. No. 10/804,031 filed Mar. 19, 2004, now U.S. Pat. No. 7,175,610, which claims priority of Japanese patent application No. 2003-078867 filed Mar. 20, 2003, each of which is incorporated herein by reference.

FIELD OF THE INVENTION

The present invention relates to a protector sheath for a winged needle and, more specifically, to a protector sheath which can accommodate the needle tube and the blade edge of the winged needle by being slid from the proximal side of the winged needle in order to prevent a pricking accident caused by the winged needle after use.

DESCRIPTION OF THE RELATED ART

Conventionally, a winged needle and a protector sheath for accommodating the needle tube and the blade edge of the winged needle have been formed as completely separate structures. The blade edge of the winged needle is firstly inserted into the inside of the protector sheath and subsequently the needle tube is inserted to protect the needle tube and the blade edge. Thus, use of such protector sheath has resulted in frequent occurrences of so-called inadvertent pricking accidents, in which the fingers holding the protector sheath are pricked by the blade edge, which leads to a danger of medical personnel being infected with AIDS, hepatitis, etc.

In order to prevent such inadvertent pricking accidents, a number of slide-type protectors have been developed. In one example of such protectors, a protector sheath with a slit is arranged on a tube connected to the proximal side of a winged needle, the protector sheath being slid to the distal side after the use of the winged needle to accommodate the needle tube and the blade edge of the winged needle in the protector sheath (see, for example, Japanese Patent No. 2673682).

The above-described protector sheath has in its side wall a slit or slits into which the wings of the winged needle are to be inserted. The needle tube and the blade edge of the winged needle can be easily protected only by sliding the protector sheath to the distal side. It is to be noted, however, that the slit is formed as a straight slit parallel to the axis of the protector sheath, and the winged needle is arranged in the axial direction of the protector, so that the slit and the needle tube of the winged needle are arranged parallel to each other. In a protector in which the slit and the needle tube are thus arranged, there is such a danger that the needle tube and the blade edge accommodated in the protector sheath may stick out of the slit depending upon the movement of the winged needle or of the tube connected to the proximal side of the winged needle.

Apart from this protector sheath, the following are proposed examples of a protector-capable of preventing the needle tube and the edge of a winged needle from sticking out of the slit: a protector equipped with a lock mechanism adapted to close the slit and the distal aperture after accommodation of the winged needle (see, for example, Japanese Unexamined Patent Publication No. 6-63137); a winged needle in which the hub of the winged needle also serves as the protector, thereby eliminating the need to provide a slit for wing insertion (see, for example, Japanese Unexamined Patent Publication No. 7-75671); and a protector in which the proximal end portion of the slit of the protector is provided so as to extend in a direction which is not parallel to the axial direction of the protector, thereby making it possible to arrange the accommodated needle tube at a position deviated from the axial center of the protector (see, for example, U.S. Pat. No. 5,772,638).

However, in the above-mentioned protector equipped with said lock mechanism adapted to close the slit, the lock mechanism should necessarily prevent the needle tube and the edge of the winged needle from sticking out of the slit, which involves a complicated construction and difficult molding.

In the winged needle in which the hub also serves as the protector, the hub itself becomes relatively large, so that it is rather poor in operability for medical personnel. Further, the fixation of the winged needle to the patient by means of the wings is difficult to perform.

In the protector in which the needle tube is accommodated so as to be arranged at a position deviated from the axial direction of the protector, there is no danger of the needle tube and the edge of the winged needle sticking out of the slit. However, depending upon the movement of the winged needle or the tube connected to the proximal side thereof, there is such a danger that the blade edge of the needle tube may stick into the inner wall of the protector. Thus, in some cases, there is such a danger that the blade edge pierces through the side wall of the protector and sticks out.

It is accordingly an object of the present invention to provide a protector sheath for a winged needle which is of a simple structure and ensures satisfactory operability, and which can be easily attached to the patient and involves no danger of the needle tube and the edge of the accommodated winged needle sticking out of the sheath.

BRIEF SUMMARY OF THE INVENTION

After various careful reviews, the present inventor has found out that it is possible to achieve the above object with a protector sheath in which a slit is provided in the side all of the cylindrical main body of the protector sheath, and a proximal end portion of the slit is provided so as to extend parallel to the axis of the main body of the protector sheath and a distal end portion of the slit is provided so as to extend in a direction which is not parallel to the direction of the cylindrical main body, thus realizing the present invention.

That is, the present invention relates to:

(1) a protector sheath for a winged needle capable of accommodating a winged needle having a needle tube with a sharp blade edge, a hub firmly attached to a proximal end portion of the needle tube, and a wing provided on the hub, wherein the protector sheath has a cylindrical main body, at least one slit is provided in a side wall of the main body, a proximal end portion of the slit is configured such that it receives the wing so as to be able to arrange the needle tube of the winged needle parallel to the axis of the main body, and a distal end portion of the slit is provided so as to extend in a direction which is not parallel to the axial direction of the main body;

(2) a protector sheath for a winged needle according to item (1) wherein the slit comprises a proximal end portion having a slot with a closed end capable of accommodating the wing and arrange the needle tube of the winged needle parallel to the axis direction of the main body, a middle portion parallel to the axis direction of the main body and a distal end portion having a slit with a shallow V shape or an arched shape in the axial direction of the main body and capable of accommodating the blade edge of the needle tube.

(3) a protector sheath for a winged needle according to item (1), wherein the proximal end portion of the slit is provided parallel to the axis of the main body.

(4) a protector sheath for a winged needle according to item (1), wherein the proximal end portion of the slit constitutes only the portion where the wing is arranged when the winged-needle is accommodated in the protector sheath.

(5) a protector sheath for a winged needle according to item (1), wherein the distal end portion of the slit constitutes only the portion where the blade edge of the needle tube is arranged when the winged-needle is accommodated in the protector sheath.

(6) a protector sheath for a winged needle according to item (1), wherein the slit further has a means capable of effecting positioning of the wing at the position where the winged needle is accommodated in the protector sheath.

(7) a protector sheath for a winged needle according to item (6), wherein the means capable of effecting positioning of the wing is formed by enlarging the width solely of the portion of the slit where the wing is arranged.

(8) a protector sheath for a winged needle according to item (6), wherein the means capable of effecting positioning of the wing is a protrusion formed on the distal side of the portion of the slit where the wing is arranged.

(9) a protector sheath for a winged needle according to item (1), wherein the distal end portion of the slit is formed so as to extend in a direction that is not parallel to the axial direction of the main body.

(10) a protector sheath for a winged needle according to any one of items (1) to (9), wherein the distal end portion of the slit where the slit undergoes a change in direction is formed so as to be gently curved.

(11) a protector sheath for a winged needle according to any one of items (1) to (10), wherein the main body is connected to a holder having a proximal aperture at the proximal end portion.

(12) a protector sheath for a winged needle according to any one of items (1) to (11), wherein the most distal end of the slit is outwardly flared to form a distal aperture in the main body.

DETAILED DESCRIPTION OF THE INVENTION

Preferred embodiments of the protector of the present invention will be described in detail with reference to the accompanying drawings. The following descriptions, however, should not be restrictively construed.

Figure 1:
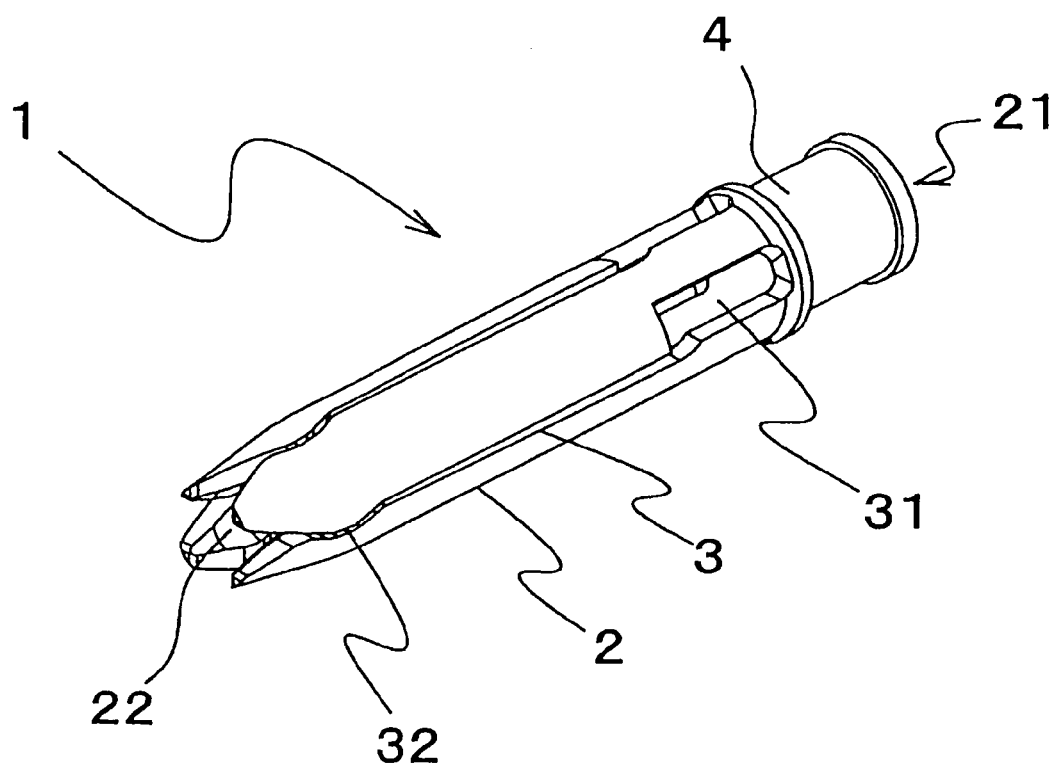
FIG. 1 is a perspective view of a protector sheath for a winged needle according to an embodiment of the present invention.
Figure 2:
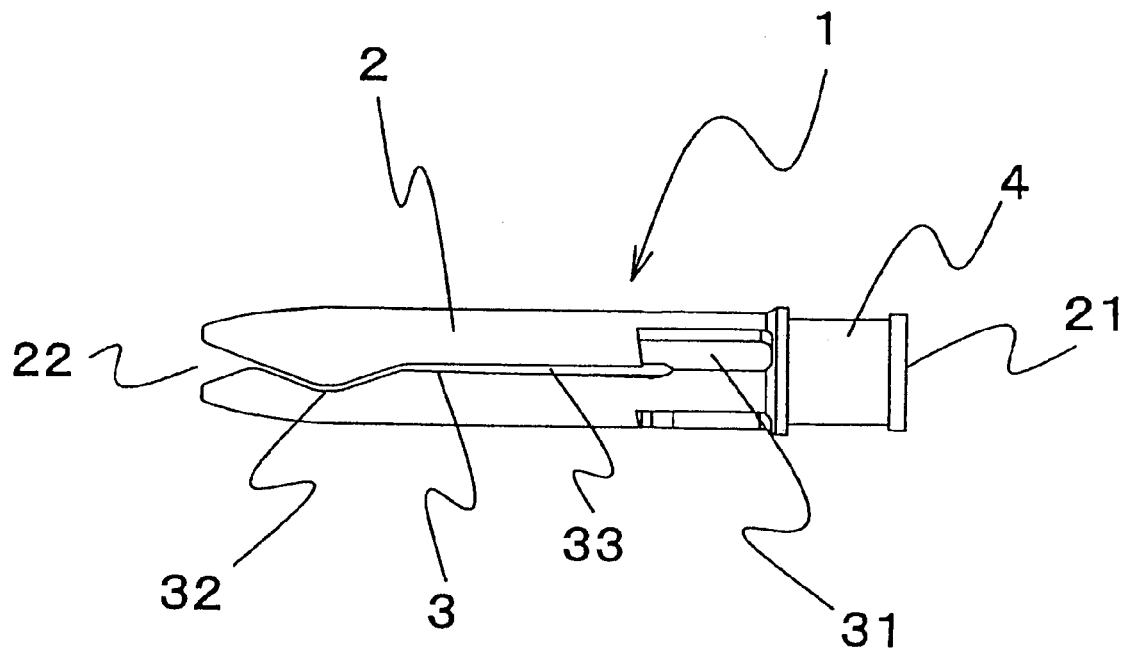
FIG. 2 is a side view of the protector sheath shown in FIG. 1.

As shown in FIGS. 1 and 2, a protector 1 according to the present invention has a cylindrical main body 2. An inner diameter of a distal end portion of the main body 2 is large enough to allow the hub and the needle tube of a winged needle to be inserted therein, and an inner diameter of the proximal end portion of the main body 2 is large enough to allow a tube connected to the proximal side of the winged needle to be inserted therein.

The main body 2 typically has a length longer than that of the winged needle, preferably, about 10 to 20 mm longer than that of the winged needle, and the wall thickness of the main body 2 is preferably, about 5 to 20 mm.

Figure 6:
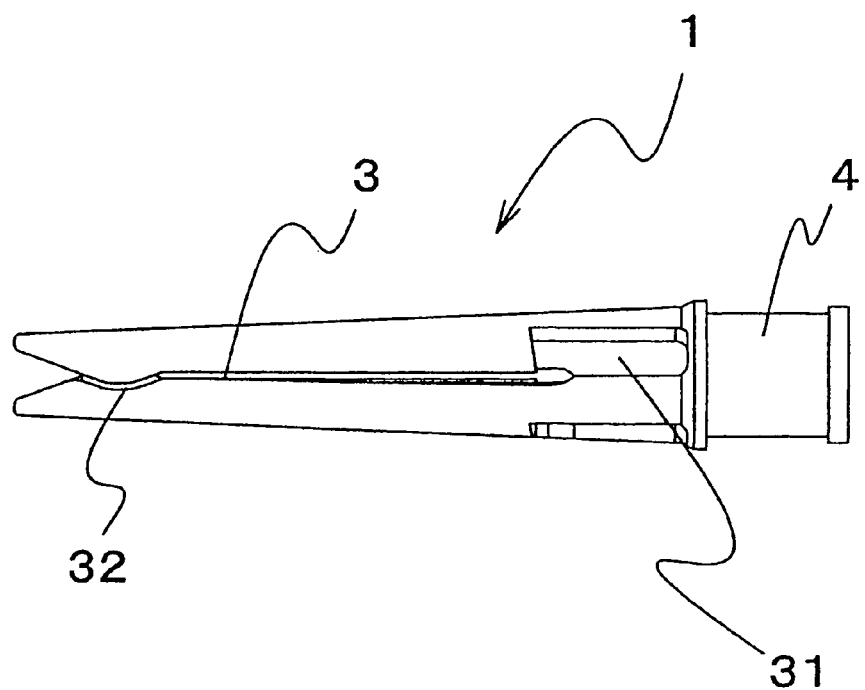
FIG. 6 is a side view of a protector sheath for a winged needle according to another embodiment of the present invention.

The main body 2 may have a tapered configuration in which outer and inner diameters of the main body 2 decrease toward the distal end (FIG. 6), or only its distal end portion may be tapered so as to decrease in diameter toward the distal end (FIG. 1 to 4). The main body 2 also has a distal aperture 22 tapered toward the distal end in the axis direction of the main body 2 and, preferably, outwardly flared. A holder 4 is connected to the proximal end portion of the main body 2 and has a proximal aperture 21.

The main body 2 is molded from a flexible material easily deformable by external forces, for example, a thermoplastic resin, such as polypropylene, polystyrene, polyacetal, polycarbonate, or acrylonitrile-butadiene-styrene copolymer or the like.

A slit 3 allowing insertion of the wings 51 of a winged needle 5 is provided in the side wall of the main body 2. The number of the slit 3 is at least one, preferably, 3 to 5. The slit 3 has a proximal end portion 31 configured such that it can receive the wings 51 so as to allow the needle tube 52 of the winged needle 5 to be arranged parallel to the axis of the main body 2. The proximal end portion is provided, for example, so as to extend parallel to the axis of the main body 2 (see FIGS. 1 to 4). When the needle tube 52 and the blade edge 53 of the winged needle 5 are to be accommodated in the protector 1, the wings 51 of the winged needle 5 enter the slit or slits 3 from the distal side thereof, i.e., distal aperture 22, and are arranged in that portion of the proximal end portion 31 which is parallel to the axis (see FIGS. 4(a) and 4(b)). Since the proximal end portion 31 is parallel to the axis of the main body 2, the needle tube 52 accommodated in the protector 1 is also arranged parallel to the axis of the main body 2.

The slit 3 has a distal end portion 32 provided so as to extend in a direction that is not parallel to the axial direction of the main body 2. The wings 51 entering the slit 3 from the distal side thereof undergo a change in direction at the boundary between the distal end portion 32 and the proximal end portion 31, preferably, the middle portion 33 of the slit 3. However, since the main body 2 is formed of a flexible material, the wings 51 can reach the proximal end portion 31 of the slit 3 as they push the distal end portion 32 in the axial direction and open the slit 3.

Figure 3:
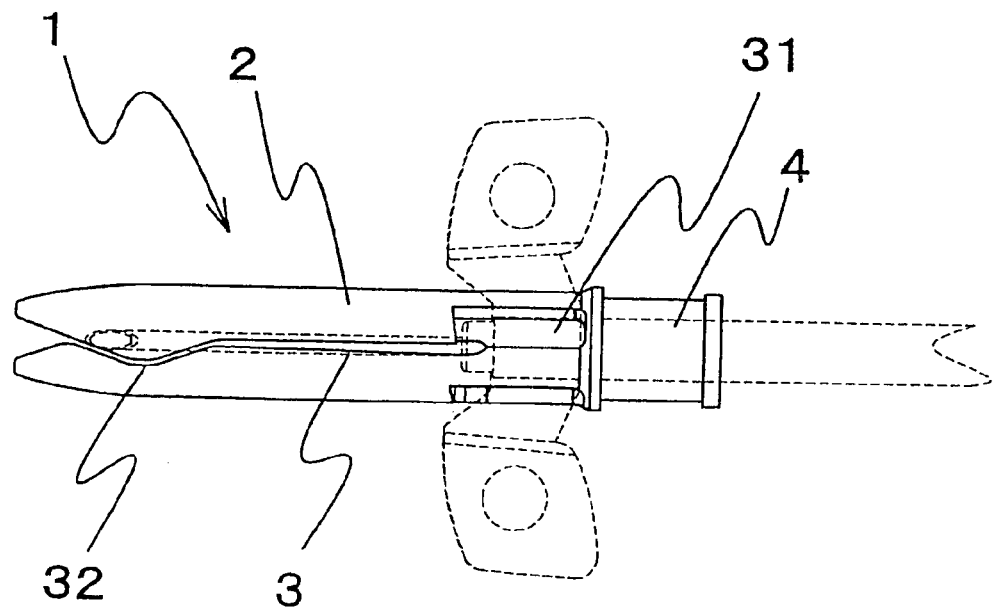
FIG. 3 is an explanatory view showing the state in which a winged needle is accommodated in the protector sheath shown in FIG. 1.
Figure 4A:
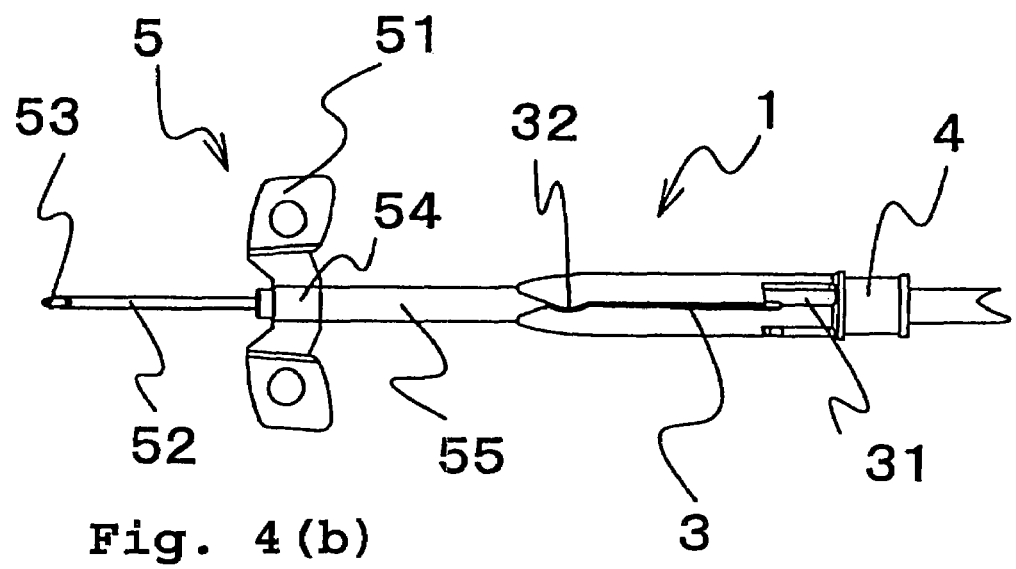
FIG. 4(a) is an explanatory view showing the state before a winged needle is accommodated in the protector sheath shown in FIG. 1
Figure 4B:
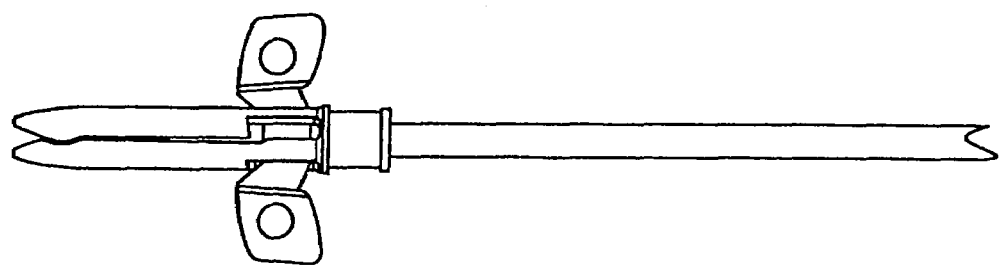
FIG. 4(b) is an explanatory view showing the state after a winged needle is accommodated in the protector sheath shown in FIG. 1.

As shown in FIG. 3, the needle tube 52 accommodated in the protector 1 is arranged parallel to the axis of the main body 2, so that the blade edge 53 of the needle tube 52 is not arranged parallel to the distal end portion 32 of the slit 3. Thus, there is no danger of the blade edge 53 of the needle tube 52 sticking out of the distal end portion 32 of the slit 3 when the needle tube 52 is moved.

Figure 5:
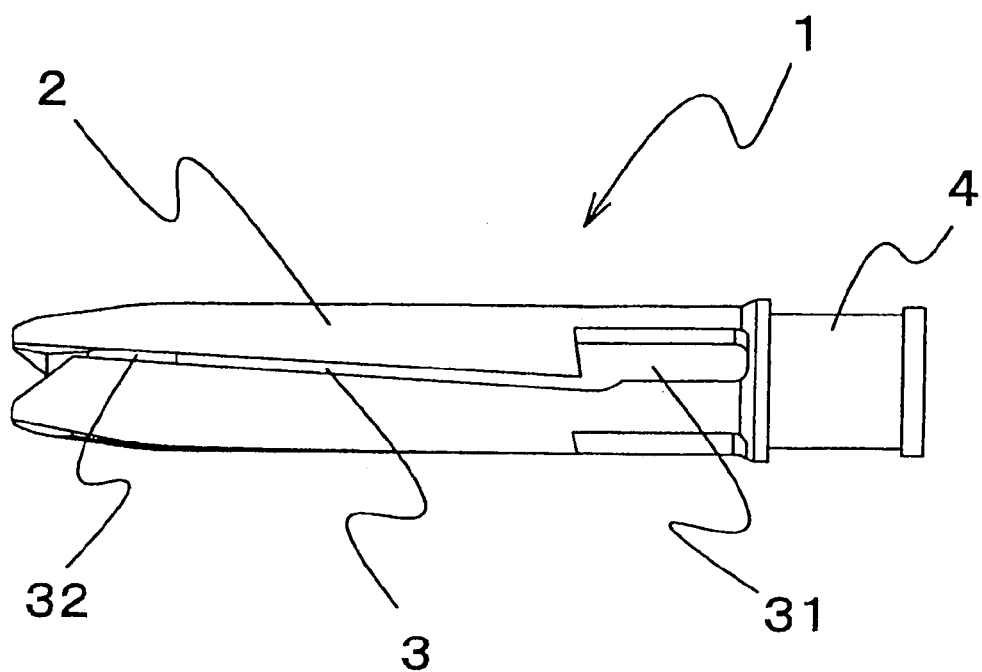
FIG. 5 is a side view of a protector sheath for a winged needle according to another embodiment of the present invention.

As shown in FIGS. 1 through 4, regarding the configuration of the slit 3, the distal end portion 32, provided so as to extend in a direction that is not parallel to the axial direction of the main body 2, may constitute solely the portion where the blade edge 53 of the needle tube 52 is arranged when the winged needle 5 is accommodated in the protector 1, the remaining portion of the slit constituting the proximal end portion 31 that is parallel to the axis. Conversely, as shown in FIG. 5, the proximal end portion 31, provided so as to be parallel to the axis of the main body 2, may constitute solely the portion where the wings 51 are arranged when the winged needle 5 is accommodated in the protector 1, the remaining portion constituting the distal end portion 32 extending in a direction that is not parallel to the axial direction. The distal end portion 32 and preferably, a middle portion 33, may be angled relative to the axis of the main body 2 at an angle of 5 to 30°, preferably, 10 to 20° (see FIG. 6).

Figure 7:
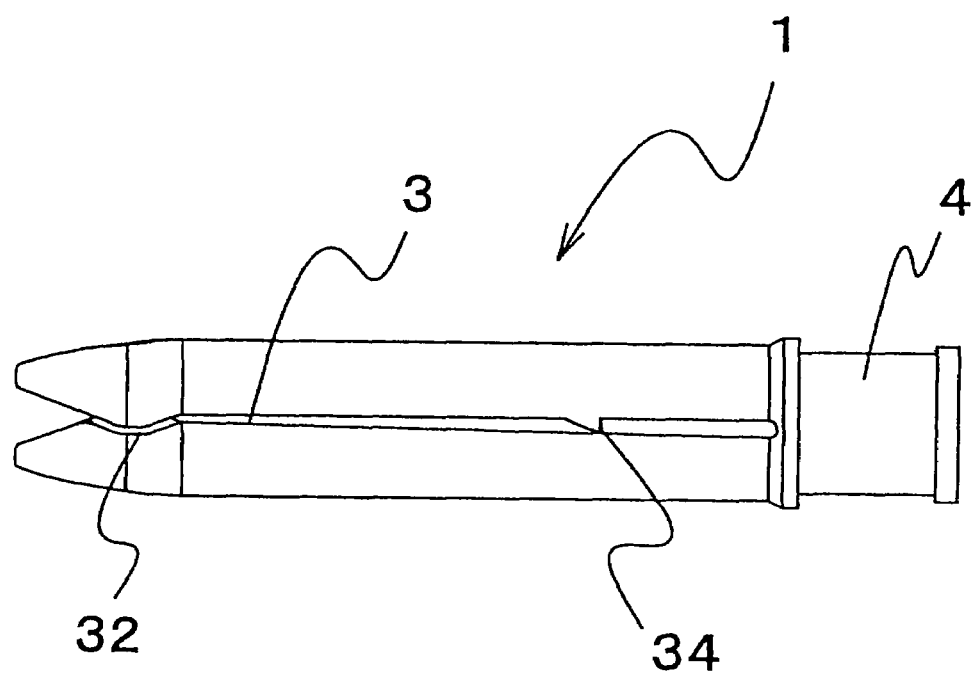
FIG. 7 is a side view of a protector sheath for a winged needle according to a further embodiment of the present invention.

While there are no particular limitations regarding the configuration of the proximal end portion 31 of the slit 3, which is provided so as to be parallel to the axis of the sheath body, the proximal end portion 31 desirably has a mechanism capable of effecting positioning of the wings at a position that allows the needle tube to be completely accommodated in the protector 1. More specifically, as shown in FIGS. 1 through 5, it is possible to adopt a configuration in which the width of the slit 3 is enlarged only in a portion thereof to form a slot where the wings 51 are arranged, or as shown in FIG. 7, a configuration in which a protrusion 34 capable of preventing the wings 51 from returning to the distal side is formed on the distal side of the proximal end portion 31 of the slit 3 where the wings 5 are arranged.

The distal end portion 32 of the slit 3, provided so as to extend in a direction not parallel to the axis of the protector sheath, may have such a configuration to have a certain angle with respect to the axis direction to a degree so that the edge of the needle tube accommodated in the protector 1 does not stick out. Thus, it is possible, as shown in FIG. 5, to form a linear slit which is at a fixed angle with respect to the axis so as to form a middle portion and a distal end portion, or, as shown in FIGS. 1 through 4, to form a plurality of consecutive linear slits that are at fixed angles with respect to the axis, for example, a shallow V shape, or an arched shape. Regarding the portion where the slit direction changes, it is desirable to form the portion as a gently curved slit so that resistance to entry of the wings 51 will be reduced. The distal end portion 32 of the slit 3 may have a shallow V shape or an arched shape to receive the blade edge 53 of the needle tube 52.

The slit 3 in the present invention comprises, preferably, a proximal end portion having a slot with a closed end so as to be capable of accommodating the wing 5 and of arranging the needle tube 52 of the winged needle 5 parallel to the axis of the main body 2, a middle portion parallel to the axis of the main body 2 and a distal end portion having a slit 3 with a shallow V shape or an arched shape so as to be capable of accommodating the blade edge 53 of the needle tube 52.

The protector 1 of the present invention can be mounted for use with a conventional ordinary winged needle. The conventional winged needle 5 has a needle tube 52 with a sharp blade edge 53, a hub 54 firmly attached to the proximal end portion of the needle tube 52, and wings 51 provided on the hub 54. However, the winged needle according to the present invention is not limited to one have the configurations shown in the FIGS. 1 to 7. When the winged needle 5 is to be used, a tube 55 is connected to the proximal end of the winged needle 5, and the protector 1 of the present invention is arranged on the tube 55 (see FIG. 4(*a*)). Since the protector 1 is formed of a flexible material, the inner diameter thereof can be small enough so as to be capable of holding the tube 55. Thus, when the winged needle 5 is in use, the protector 1 does not freely move on the tube 55, thus making it always possible to arrange protector 1 in a position easily allowing accommodation of the winged needle.

After use of the winged needle 5, the protector 1 of the present invention is slid forward toward the winged needle 5, whereby the wings 51 of the winged needle 5 enter the slit or slits 3 of the protector 1 from the distal side toward the proximal side, thus accommodating the needle tube 52 and the blade edge 53 of the winged needle 5 in the protector 1. The needle tube 52 accommodated in the protector 1 is arranged parallel to the axis of the main body 2, so that the blade edge 53 of the winged needle 5 is not arranged parallel to the distal end portion 32 of the slit 3, which is provided so as to extend in a direction which is not parallel to the axial direction. Thus, there is no danger of the blade edge 53 of the needle tube 52 sticking out of the slit 3 of the protector 1.

In the protector of the present invention, there is provided a slit composed of a proximal end portion provided so as to be parallel to the axis of the main body and a distal end portion provided so as to extend in a direction not parallel to the axial direction, whereby there is no fear of the needle tube and the edge of the winged needle accommodated in the protector sticking out of the slit. Further, since there is no need to provide the protector with a special mechanism for preventing the needle tube and the edge from sticking out, the protector is of a simple structure that can be easily molded. Further, the protector of the present invention can be mounted for use not only with a conventional winged needle but also a newly devised winged needle, and involves no increase in hub structure size, thereby ensuring satisfactory operability and facilitating fixing to the patient.

What is claimed is:

1. An assembly of a winged needle and a protector sheath for accommodating the winged needle, said winged needle comprising a needle tube with a sharp blade edge, a hub attached to a proximal end portion of the needle tube, a wing provided on the hub, and a flexible tube connected to the proximal end of the winged needle, and said protector sheath being slidably positioned on the flexible tube and comprising a cylindrical main body having a proximal end and a distal end, at least three slits provided in a side wall of the main body and dividing the side wall into a corresponding number of sections, and wherein each of said at least three slits comprises a proximal end portion having a slot with a closed end and capable of accommodating the wing of the winged needle, a middle portion parallel to the longitudinal axis of the main body and a curved distal end portion arranged in the side wall of the main body on the proximal side of the distal end and having a shallow V shape or an arched shape formed by a V shape or an arched shape convex portion in one of said sections and a corresponding V shape or arched shape concave portion in an adjacent section and opposite the convex portion such that the convex portion and concave portion are interfitting, the proximal end portion of the slit being configured such that it receives the wing so that the needle tube of the winged needle is arranged parallel to the longitudinal axis of the main body.

2. The assembly of a winged needle and protector sheath for accommodating the winged needle according to claim 1, wherein the proximal end portion of each of said at least three slits is provided parallel to the longitudinal axis of the main body.

3. The assembly of a winged needle and protector sheath for accommodating the winged needle according to claim 1, wherein the proximal end portion of each of said at least three slits constitutes only the portion where the wing is arranged when the winged-needle is accommodated in the protector sheath.

4. The assembly of a winged needle and protector sheath for accommodating the winged needle according to claim 1, wherein the distal end portion of each of said at least three slits constitutes only the portion where the blade edge of the needle Lube is arranged when the winged needle is accommodated in the protector sheath.

5. The assembly of a winged needle and protector sheath for accommodating the winged needle according to claim 1, wherein each of said at least three slits further comprises a means capable of effecting positioning of the wing at the position where the winged needle is accommodated in the protector sheath.

6. The assembly of a winged needle and protector sheath for accommodating the winged needle according to claim 5, wherein the means capable of effecting positioning of the wing is formed by enlarging the width of the portion of each of said at least three slits where the wing is arranged.

7. The assembly of a winged needle and protector sheath for accommodating the winged needle according to claim 1, wherein the V shape or arched shape convex portion and corresponding V shape or arched shape concave portion are formed so as to be gently curved.

8. The assembly of a winged needle and protector sheath for accommodating the winged needle according to claim 1, wherein the main body is connected at the proximal end portion to a holder having an aperture.

9. The assembly of a winged needle and protector sheath for accommodating the winged needle according to claim 1, wherein the distal most end of each of said at least three slits is outwardly flared.

10. The assembly of a winged needle and protector sheath for accommodating the winged needle according to claim 1, wherein the proximal end of the cylindrical main body of the protector sheath has an inner diameter sufficiently small to grip and hold the flexible tube.

* * * * *